(12) United States Patent
Nakashima et al.

(10) Patent No.: US 10,681,283 B2
(45) Date of Patent: Jun. 9, 2020

(54) IMAGING SYSTEM, IMAGING APPARATUS, AND IMAGING METHOD

(71) Applicant: SONY CORPORATION, Tokyo (JP)

(72) Inventors: Yusaku Nakashima, Tokyo (JP); Tetsuro Kuwayama, Tokyo (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/070,347

(22) PCT Filed: Nov. 18, 2016

(86) PCT No.: PCT/JP2016/085081
§ 371 (c)(1),
(2) Date: Jul. 16, 2018

(87) PCT Pub. No.: WO2017/134907
PCT Pub. Date: Aug. 10, 2017

(65) Prior Publication Data
US 2019/0068861 A1    Feb. 28, 2019

(30) Foreign Application Priority Data

Feb. 3, 2016    (JP) .................................. 2016-019057

(51) Int. Cl.
*H04N 5/235*    (2006.01)
*H04N 9/04*    (2006.01)
(Continued)

(52) U.S. Cl.
CPC ........... *H04N 5/235* (2013.01); *H04N 5/2256* (2013.01); *H04N 5/2354* (2013.01); *H04N 9/04551* (2018.08); *A61B 1/04* (2013.01)

(58) Field of Classification Search
CPC .. H04N 5/235; H04N 9/04551; H04N 5/2256; A61B 1/04
See application file for complete search history.

(56) References Cited

U.S. PATENT DOCUMENTS

| | | | |
|---|---|---|---|
| 8,502,926 B2 * | 8/2013 | Bilbrey | H04N 5/74 348/744 |
| 2014/0055661 A1 | 2/2014 | Imamura et al. | |
| 2016/0262622 A1 | 9/2016 | Ishihara | |

FOREIGN PATENT DOCUMENTS

| | | |
|---|---|---|
| CN | 103460024 A | 12/2013 |
| CN | 105764401 A | 7/2016 |

(Continued)

OTHER PUBLICATIONS

International Search Report and Written Opinion of PCT Application No. PCT/JP2016/085081, dated Feb. 7, 2017, 09 pages of ISRWO.

*Primary Examiner* — Twyler L Haskins
*Assistant Examiner* — Angel L Garces-Rivera
(74) *Attorney, Agent, or Firm* — Chip Law Group (57) ABSTRACT

There is provided an imaging technology using a speckle, which is capable of eliminating cross-talk. In the present technology, there is provided an imaging system including: a first light source that irradiates an imaging target with coherent light of a first wavelength band; a second light source that irradiates the imaging target with incoherent light of a second wavelength band; an image capturing unit that captures a speckle image and a non-speckle image, the speckle image being obtained from scattered light of the imaging target irradiated with the coherent light, the non-speckle image being obtained from reflected light of the imaging target irradiated with the incoherent light; and a cross-talk elimination unit that eliminates cross-talk that occurs between the captured speckle image and the captured non-speckle image.

26 Claims, 5 Drawing Sheets

(51) Int. Cl.
*H04N 5/225* (2006.01)
*A61B 1/04* (2006.01)

(56) References Cited

FOREIGN PATENT DOCUMENTS

| | | |
|---|---|---|
| JP | 2014-108193 A | 6/2014 |
| JP | 2015-216978 A | 12/2015 |
| WO | 2013/114891 A1 | 8/2013 |
| WO | 2015/080215 A1 | 6/2015 |
| WO | 2015/174289 A1 | 11/2015 |

* cited by examiner

IMAGING SYSTEM, IMAGING APPARATUS, AND IMAGING METHOD

CROSS REFERENCE TO RELATED APPLICATIONS

This application is a U.S. National Phase of International Patent Application No. PCT/JP2016/085081 filed on Nov. 18, 2016, which claims priority benefit of Japanese Patent Application No. JP 2016-019057 filed in the Japan Patent Office on Feb. 3, 2016. Each of the above-referenced applications is hereby incorporated herein by reference in its entirety.

TECHNICAL FIELD

The present technology relates to an imaging system, an imaging apparatus, and an imaging method. More specifically, the present technology relates to an imaging system, an imaging apparatus, and an imaging method that use a speckle generated by irradiating an imaging target with light.

BACKGROUND ART

In general, a method of acquiring an X-ray image by injecting a contrast medium into the blood vessels is used for checking the state and position of blood vessels in the body. Further, in recent years, an angiography method such as a computed tomography (CT) angiography and a magnetic resonance angiography (MRA) by which a three-dimensional image can be acquired has also been developed.

Further, a method of imaging a flow path such as a blood vessel by using an optical method has also been proposed (see Patent Literature 1) in the past. In the imaging system described in Patent Literature 1, an interference light image is captured at a first timing by light that is reflected on an object and interfered, which is emitted from a light emitting unit, and a luminescent image is captured at a second timing by light emitted from the object.

As described above, in recent years, in the medical field and the like, various imaging methods using optical methods have been developed, and the detection accuracy thereof is also improved year by year. Here, in the imaging technology using an optical method, there is a concern that occurrence of various types of noise reduces the detection accuracy, and a speckle is known as one of such noise. The speckle is a phenomenon in which a spotty swaying pattern appears on an irradiation surface in accordance with the uneven shape of the irradiation surface. In recent years, technologies relating to a method of imaging a flow path such as a blood vessel by using a speckle that is one of such noise are also being developed.

Here, the speckle is a random interference/diffraction pattern due to scattering or the like in an optical path. Further, the magnitude of the speckle is represented by an index called a speckle contrast that is a value obtained by dividing the standard deviation of the intensity distribution by the average of the intensity distribution. When an object illuminated with coherent light is observed using an imaging optical system, a speckle due to scattering of the object is observed on the image surface. Then, when the object moves or the shape of the object changes, a random speckle pattern corresponding thereto is observed.

When a light scattering fluid such as blood is observed, the speckle pattern changes by the change in the fine shape due to flow as time passes. At that time, when an image sensor is placed on the image surface and a fluid is imaged with an exposure time sufficiently longer than the change of the speckle pattern, the speckle contrast of a part where blood is flowing, i.e., a part of blood vessels, is reduced by time averaging. By using such a change in the speckle contrast, angiography can be performed.

CITATION LIST

Patent Literature

Patent Literature 1: Japanese Patent Application Laid-open No. 2009-136396

DISCLOSURE OF INVENTION

Technical Problem

In such an imaging technology using a speckle, an image sensor in which monochrome pixels are arranged as pixels is usually used for capturing a speckle image. However, for example, when illumination is RGB illumination as in the case of white illumination for capturing a normal bright field image, there has been a problem that green cross talk affects the device that images the speckle and a speckle image cannot be captured appropriately.

In view of the above, it is a main object of the present technology to provide an imaging technology using a speckle, which is capable of eliminating cross-talk.

Solution to Problem

The present technology provides an imaging system, including: a first light source that irradiates an imaging target with coherent light of a first wavelength band; a second light source that irradiates the imaging target with incoherent light of a second wavelength band; an image capturing unit that captures a speckle image and a non-speckle image, the speckle image being obtained from scattered light of the imaging target irradiated with the coherent light, the non-speckle image being obtained from reflected light of the imaging target irradiated with the incoherent light; and a cross-talk elimination unit that eliminates cross-talk that occurs between the captured speckle image and the captured non-speckle image.

In the imaging system according to the present technology, the first light source may be a red light source, and the second light source may be a blue light source.

Further, in the imaging system according to the present technology, the wavelength band of the coherent light may be 550 to 700 nm, and the wavelength band of the incoherent light may be 350 to 550 nm.

Further, in the imaging system according to the present technology, the second light source may irradiate the imaging target with the incoherent light simultaneously with the irradiation by the first light source.

Further, in the imaging system according to the present technology, a separation unit that separates the captured speckle image and the captured non-speckle image may be provided.

Further, in the imaging system according to the present technology, an image combination unit that combines the separated speckle image and the separated non-speckle image may be provided.

Further, in the imaging system according to the present technology, the cross-talk elimination unit may be a pixel unit in which pixels corresponding to respective color components including a plurality of color components are regularly arranged on a plane.

Further, in the imaging system according to the present technology, the cross-talk elimination unit may have a Bayer pattern.

The present technology provides also an imaging apparatus including: a first light source that irradiates an imaging target with coherent light of a first wavelength band; a second light source that irradiates the imaging target with incoherent light of a second wavelength band; an image capturing unit that captures a speckle image and a non-speckle image, the speckle image being obtained from scattered light of the imaging target irradiated with the coherent light, the non-speckle image being obtained from reflected light of the imaging target irradiated with the incoherent light; and a cross-talk elimination unit that eliminates cross-talk that occurs between the captured speckle image and the captured non-speckle image.

In the imaging apparatus according to the present technology, the first light source may be a red light source, and the second light source may be a blue light source.

Further, in the imaging apparatus according to the present technology, the wavelength band of the coherent light may be 550 to 700 nm, and the wavelength band of the incoherent light may be 350 to 550 nm.

Further, in the imaging apparatus according to the present technology, the second light source may irradiate the imaging target with the incoherent light simultaneously with the irradiation by the first light source.

Further, in the imaging apparatus according to the present technology, a separation unit that separates the captured speckle image and the captured non-speckle image may be provided.

Further, in the imaging apparatus according to the present technology, an image combination unit that combines the separated speckle image and the separated non-speckle image may be provided.

Further, in the imaging apparatus according to the present technology, the cross-talk elimination unit may be a pixel unit in which pixels corresponding to respective color components including a plurality of color components are regularly arranged on a plane.

Further, in the imaging apparatus according to the present technology, the cross-talk elimination unit may have a Bayer pattern.

The present technology provides also an imaging method including: a coherent light irradiation step of irradiating an imaging target with coherent light of a first wavelength band; an incoherent light irradiation step of irradiating the imaging target with incoherent light of a second wavelength band; a speckle image capturing step of capturing a speckle image obtained from scattered light of the imaging target irradiated with the coherent light; a non-speckle image capturing step of capturing a non-speckle image obtained from reflected light of the imaging target irradiated with the incoherent light; and a cross-talk elimination step of eliminating cross-talk that occurs between the captured speckle image and the captured non-speckle image.

In the imaging method according to the present technology, the coherent light may be red light, and the incoherent light may be blue light.

Further, in the imaging method according to the present technology, the wavelength band of the coherent light may be 550 to 700 nm, and the wavelength band of the incoherent light may be 350 to 550 nm.

Further, in the imaging method according to the present technology, the coherent light irradiation step and the incoherent light irradiation step may be simultaneously performed.

Further, in the imaging method according to the present technology, a separation step of separating the captured speckle image and the captured non-speckle image may be provided.

Further, in the imaging method according to the present technology, an image combination step of combining the separated speckle image and the separated non-speckle image may be provided.

Advantageous Effects of Invention

In accordance with the present technology, since cross-talk can be eliminated, it is possible to capture a sharper speckle image.

It should be noted that the effect described here is not necessarily limitative and may be any effect described in the present technology.

MODE(S) FOR CARRYING OUT THE INVENTION

Hereinafter, favorable embodiments for carrying out the present technology will be described with reference to the drawings. The embodiments described below illustrate only examples of typical embodiments of the present technology, and the scope of the present technology is not narrowly interpreted by the embodiments. Note that description will be made in the following order.

Figure 1:
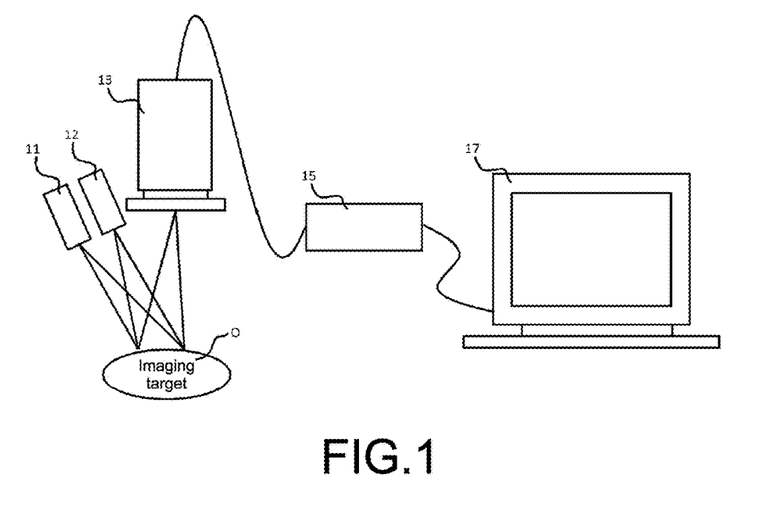
FIG. 1 is a conceptual diagram schematically showing a first embodiment of an imaging system according to the present technology.
Figure 2:
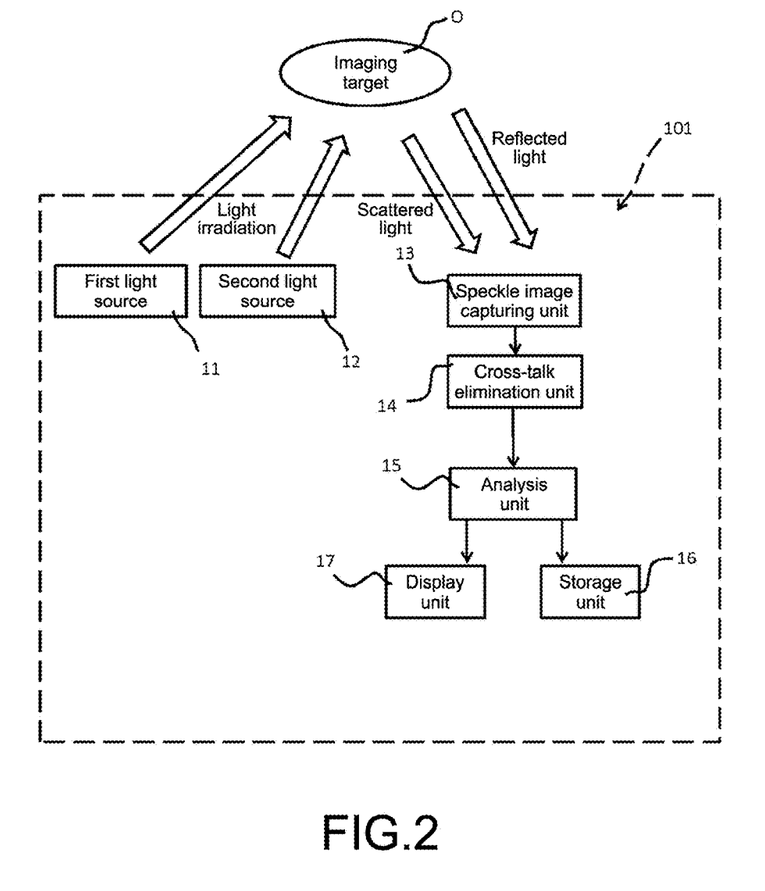
FIG. 2 is a schematic conceptual diagram showing details of the imaging system shown in FIG. 1.

1. Imaging Apparatus according to First Embodiment
(1) First Light Source
(2) Second Light Source
(3) Image Capturing unit
(4) Cross-Talk Elimination Unit
(5) Analysis Unit
(6) Storage Unit
(7) Display Unit
(8) Imaging Target
2. Imaging Apparatus according to Second Embodiment
(1) Separation Unit
(2) Speckle Processing Unit
(3) Speckle Image Processing Unit
(4) Non-speckle image Processing Unit
(5) Image Combination Unit 3. Imaging Apparatus
 (1) First Light Source
 (2) Second Light Source
 (3) Image Capturing unit
 (4) Cross-Talk Elimination Unit
 (5) Analysis Unit
 (6) Storage Unit
 (7) Display Unit
4. Imaging Method
 (1) Coherent Light Irradiation Step
 (2) Incoherent Light Irradiation Step
 (3) Image Capturing Step
 (4) Cross-Talk Elimination Step
 (5) Separation Step
 (6) Speckle Processing Step
 (7) Speckle Image Processing Step
 (8) Non-speckle image Processing Step
 (9) Image Combination Step
 (10) Analysis Step
 (11) Storage Step
 (12) Display Step 1. Imaging Apparatus According to First Embodiment FIG. 1 is a schematic conceptual diagram schematically showing a first embodiment of an imaging system according to the present technology. An imaging system 101 according to a first embodiment roughly includes at least a first light source 11, a second light source 12, an image capturing unit 13, and a cross-talk elimination unit 14. Further, as necessary, it may further include an analysis unit 15, a storage unit 16, a display unit 17, and the like. Hereinafter, the respective units will be described in detail.

(1) First Light Source

The first light source 11 irradiates an imaging target O with coherent light. The coherent light emitted from the first light source 11 represents light in which the phase relationship of light waves at arbitrary two points in the light beam temporally invariable and constant, which shows perfect coherence even when after the light beam is split by an arbitrary method, a large optical path difference is given to the split light beams and the light beams are overlapped again. It is preferable that the coherent light output from the first light source 11 according to the present technology has a wavelength band in the range of 550 to 700 nm and is red. It is more preferable that the coherent light has a wavelength band of 600 nm and is red.

The type of the first light source 11 that emits the coherent light is not particularly limited as long as the effect of the present technology is not impaired. Examples thereof include laser light. As the first light source 11 that emits laser light, for example, one or more kinds of an argon ion (Ar) laser, a helium-neon (He—Ne) laser, a dye laser, a krypton (Cr) laser, a semiconductor laser, a solid laser obtained by combining a semiconductor laser and a wavelength conversion optical device, and the like can be freely combined and used.

(2) Second Light Source

The second light source 12 irradiates the imaging target O with incoherent light. In the imaging system according to the present technology, coherent light and incoherent light are simultaneously applied to the imaging target O. That is, the second light source 12 and the first light source 11 simultaneously apply light. The incoherent light emitted from the second light source 12 is light that hardly shows coherence like object light (object wave).

It is preferable that the incoherent light output from the second light source 12 according to the present technology has a wavelength band in the range of 350 to 550 nm and is blue. It is more preferable that the incoherent light has a wavelength band of 400 nm and is blue.

The type of the second light source 12 is not particularly limited as long as the effect of the present technology is not impaired. Examples thereof include a light emitting diode. Further, examples of another light source include a xenon lamp, a metal halide lamp, and a high pressure mercury lamp.

(3) Image Capturing Unit

The image capturing unit 13 captures a speckle image and a non-speckle image.

That is, the image capturing unit 13 images a speckle based on scattered light obtained from the imaging target O irradiated with the coherent light. Further, the imaging target O is imaged on the basis of reflected light obtained from the imaging target O irradiated with the incoherent light. Here, since the incoherent light is light that hardly shows coherence, a speckle that is a random interference/diffraction pattern does not occur in the captured image based on the incoherent light. Hereinafter, the captured image in which no speckle occurs will be referred to as "non-speckle image" for convenience of description.

Further, in the image capturing unit 13, the brightness distribution of the speckle in the captured speckle image may be measured. Here, when an object illuminated by using the coherent light is observed by an imaging optical system, a speckle due to scattering of the object is observed on the image surface. In this image capturing unit 13, for example, the brightness distribution of the speckle in the captured image is measured using a brightness meter. In addition, the brightness distribution of the speckle can be calculated from an image captured by an image sensor such as CCD and CMOS.

This method of measuring the brightness distribution is not particularly limited as long as the effect of the present technology is not impaired, and one or more kinds of known calculation methods can be selected and freely used in combination.

Such an imaging method performed by the image capturing unit 13 is not particularly limited as long as the effect of the present technology is not impaired, and one or more kinds of known imaging methods can be selected and freely used in combination. Examples of the imaging method include an imaging method using an image sensor such as a CCD (Charge Coupled Device) sensor and a CMOS (Complementary Metal Oxide Semiconductor) sensor.

In this image capturing unit 13, for example, an image or the like in which pseudo blood vessels through which pseudo blood is flowing are mapped on the basis of the brightness distribution of the speckle is generated. Here, since the speckle is a random interference/diffraction pattern as described above, when a scattering fluid such as blood moves or temporarily changes, also the speckle temporarily changes. Therefore, it is possible to observe the boundary between the fluid and other parts.

Note that the image capturing unit 13 may be configured to perform leveling using a plurality of speckle images, for example, to reduce the unevenness of the speckle image in order to clarify the part where a speckle occurs.

(4) Cross-Talk Elimination Unit

In the imaging system 101 according to the present technology, as described above, coherent light and incoherent light are simultaneously applied to the imaging target O, and a speckle image and a non-speckle image are captured on the basis of scattered light and reflected light from the imaging target O.

In such a case, depending on the configuration of the image sensor included in the image capturing unit 13, arranged pixels constituting the image sensor may receive stray light such as light that should have been applied to adjacent pixels in the array. That is, in the image capturing unit 13, there is a possibility that so-called cross-talk occurs.

In the cross-talk elimination unit 14, the cross-talk is eliminated.

More specifically, the cross-talk elimination unit 14 is configured as a pixel unit in which pixels corresponding to respective color components including a plurality of color components are regularly arranged on a plane, and placed closer to the imaging target O than the image capturing unit 13. Then, pixel data obtained from only pixels sensitive to light (e.g., red coherent light) of a specific wavelength is used for a speckle image, and pixel data obtained from only pixels sensitive to light (e.g., blue incoherent light) of a specific wavelength is used for a non-speckle image. Such a method can be considered. In the case where the cross-talk elimination unit 14 is configured in this way, since pixels constituting the cross-talk elimination unit 14 do not receive stray light, it is possible to eliminate cross-talk as much as possible.

Examples of the specific configuration of the cross-talk elimination unit 14 include a single plate type digital imager masked with a color filter in a Bayer pattern including pixels corresponding to color components of R, G, and B. Examples of another configuration include a three-plate type digital imager.

(5) Analysis Unit

The imaging system 101 according to the present technology can include the analysis unit 15 as necessary. In this analysis unit 15, a speckle combination image obtained by combining a speckle image and a non-speckle image from which a speckle is eliminated by the cross-talk elimination unit 14 is analyzed. Specifically, the state of the imaging target O is analyzed on the basis of the brightness distribution or speckle shown in the speckle combination image.

In the analysis unit 15, for example, in the case where the imaging target O is a blood vessel, when a scattering fluid such as blood moves or temporarily changes, also the speckle temporarily changes accordingly. Therefore, the analysis unit 15 is capable of measuring the velocity of blood flow.

Note that this analysis unit 15 is not essential to the imaging system 101 according to the present technology, and an external analysis apparatus or the like may be used to analyze the state of the imaging target O.

(6) Storage Unit

The imaging system 101 according to the present technology may include the storage unit 16 as necessary. In this storage unit 16, the speckle image and the non-speckle image captured by the image capturing unit 13, the speckle combination image, an analysis result by the analysis unit 15, and the like are stored.

This storage unit 16 is not essential to the imaging system 101 according to the present technology. For example, an external storage apparatus may be connected, and the speckle image and the like may be stored therein.

(7) Display Unit

The imaging system 101 according to the present technology may include the display unit 17 as necessary. On this display unit 17, the speckle image and the non-speckle image captured by the image capturing unit 13, the speckle combination image, an analysis result by the analysis unit 15, and the like are displayed.

Here, on the display unit 17, the brightness distribution of the speckle measured by the image capturing unit 13 may be superimposed on the speckle image and displayed.

This display unit 17 is not essential to the imaging system 101 according to the present technology. For example, an external monitor or the like may be used to irradiate the imaging target O with light.

(8) Imaging Target

The imaging system 101 according to the present technology is capable of taking various objects as imaging targets. However, the imaging system 101 can be favorably used for imaging using, for example, an object including a fluid as the imaging target O. It is difficult for the speckle to occur from a fluid due to the nature of the speckle. Therefore, by using the imaging system 101 according to the present technology for imaging an object including a fluid, the boundary between the fluid and other parts, the flow rate of the fluid, and the like can be obtained.

More specifically, the imaging target O can be a biological tissue, and the fluid can be blood. For example, by mounting the imaging system 101 according to the present technology on a surgical microscope, a surgical endoscope, or the like, it is possible to perform surgery while checking the position of blood vessels. Therefore, it is possible to perform safer and more accurate surgery, and contribute to further development of the medical technology.

In accordance with the above-mentioned imaging system 101 according to the present technology, since the cross-talk elimination unit 14 is included, it is possible to improve the resolution of the speckle image and the non-speckle image captured by the image capturing unit 13, and acquire a sharper speckle image.

As a result, for example, when blood vessels through which blood is flowing are imaged, since the speckle change according to the temporal change of blood can be observed, it is possible to acquire an image by which a flow path of blood cells can be accurately recognized. As a result, it is possible to accurately observe the relative position of blood vessels to a biological tissue (e.g., heart).

Further, in accordance with the imaging system 101 according to the present technology, since a configuration in which the speckle image and the non-speckle image are captured by the single image capturing unit 13 is adopted, for example, in the case of combining the speckle image and the non-speckle image, it is possible to eliminate occurrence of positional displacement of the respective images as much as possible. As a result, it is possible to improve the resolution of the speckle combination image, thereby making it possible to analyze the imaging target O more accurately.

Further, in accordance with the imaging system 101 according to the present technology, for example, in the case where the imaging target O is irradiated with red coherent light from the first light source 11 and a speckle image is captured on the basis of scattered light from the imaging target O, it is possible to enhance the capability of drawing blood flow when the imaging target O is blood in which scattering is dominant. Meanwhile, for example, in the case where the imaging target O is irradiated with blue incoherent light from the second light source 12 and a non-speckle image is captured on the basis of reflected light from the imaging target O, it is possible to enhance the capability of drawing blood vessels when the imaging target O is a blood vessel, because blue light is easily absorbed by the blood.

2. Imaging System According to Second Embodiment

Figure 3:
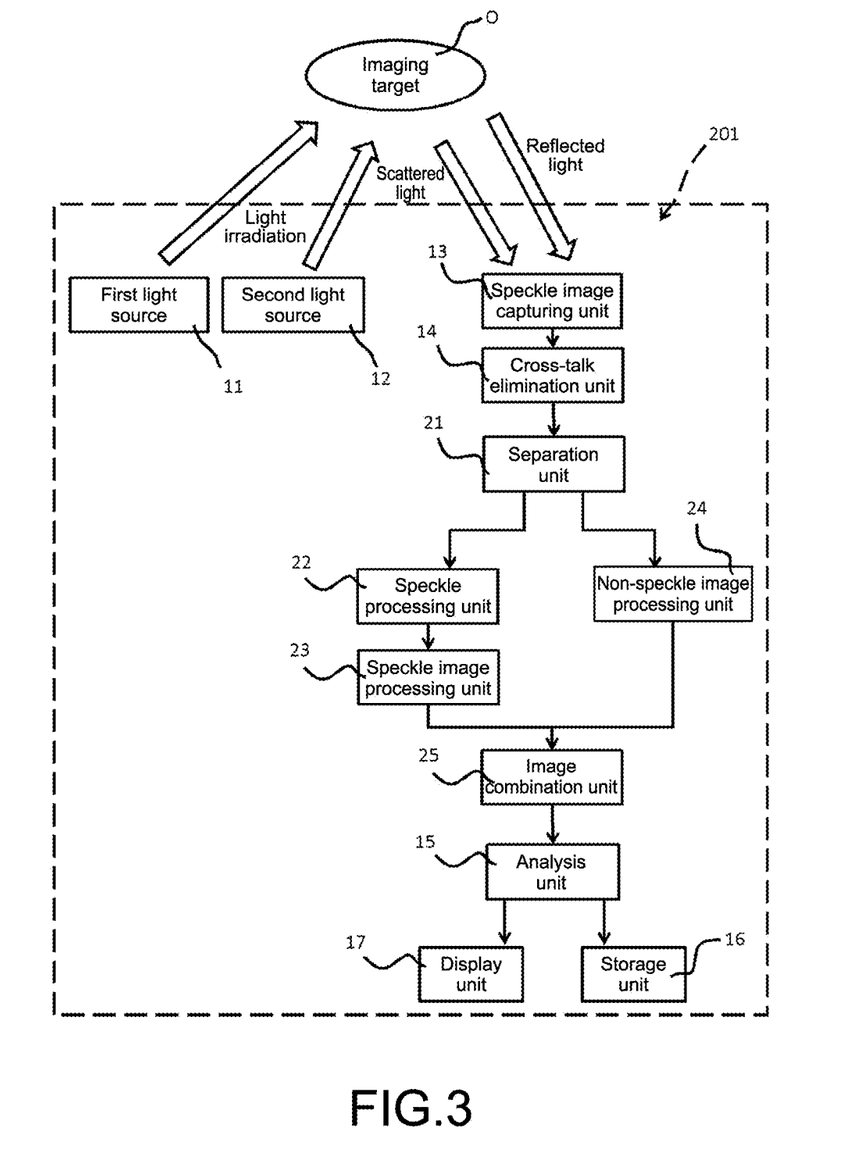
FIG. 3 is a schematic conceptual diagram schematically showing a second embodiment of the imaging system according to the present technology.

Next, a second embodiment of the imaging system according to the present technology will be described. FIG.

3 is a schematic conceptual diagram showing an imaging system 201 according to the second embodiment.

This imaging system 201 according to the second embodiment is different from the imaging system 101 according to the first embodiment in that the imaging system 201 includes a separation unit 21, a speckle processing unit 22, a speckle image processing unit 23, a non-speckle image processing unit 24, and an image combination unit 25. Meanwhile, the imaging system 201 is the same as the imaging system 101 in that the imaging system 201 includes the first light source 11, the second light source 12, the image capturing unit 13, and the cross-talk elimination unit 14 and may further include the analysis unit 15, the storage unit 16, and the display unit 17 as necessary.

Therefore, in the following description of the imaging system 201 according to the second embodiment, description of the configuration common to the imaging system 101 according to the first embodiment will be omitted. Hereinafter, the separation unit 21, the speckle processing unit 22, the speckle image processing unit 23, the non-speckle image processing unit 24, and the image combination unit 25 will be described.

(1) Separation Unit

In the imaging system according to the present technology, the image capturing unit 13 captures the speckle image and the non-speckle image, and the separation unit 21 separates image information of the captured speckle image and image information of the captured non-speckle image.

The method of separating the image information performed by the separation unit 21 is not particularly limited, and a known method can be adopted.

(2) Speckle Processing Unit

In the imaging system 201 according to the second embodiment, predetermined processing is performed on the speckle image and the non-speckle image separated by the separation unit 21.

On the speckle image, the speckle processing unit 22 and the speckle image processing unit 23 perform predetermined processing.

The speckle processing unit 22 converts the speckle image based on coherent light into a speckle fluid image in which the speckle flows in a predetermined direction. In such a case, examples of the method of calculating the flow of the speckle include a method of using, as an index, speckle contrast that is a value obtained by dividing the standard deviation of the intensity distribution by the average of the intensity distribution.

Then, in the speckle processing unit 22, a speckle fluid image is created by imaging the speckle contrast.

(3) Speckle Image Processing Unit

After a speckle fluid image is created by the speckle processing unit 22, the speckle image processing unit 23 inverts the speckle contrast in the speckle fluid image first. Here, in an image in which the speckle contrast is not inverted, the value at the point where the speckle contrast is stationary in the imaging target O is larger than that value at the point where the speckle contrast moves. Therefore, by inverting the speckle contrast, it is possible to equalize the value of the speckle image with the value at the point where the flow rate is high. Further, the speckle contrast is optimized. As a result, in the speckle fluid image, it is possible to maximize the speckle contrast, thereby making it possible to improve the detection accuracy of a scattering fluid such as blood.

Note that the method of inverting the speckle contrast and the method of optimizing the speckle contrast in the speckle image processing unit 23 are not particularly limited, and known methods can be adopted.

(4) Non-Speckle Image Processing Unit

In the imaging system 201 according to the second embodiment, after the separation unit 21 separates a non-speckle image from a speckle image, the speckle image processing unit 24 performs predetermined processing on the non-speckle image.

Specifically, the brightness distribution measured by the image capturing unit 13 is optimized. As a result, since the brightness distribution for the imaging target O can be optimized in the non-speckle image, it is possible to increase the resolution of the non-speckle image.

Note that the method of optimizing the brightness distribution by the non-speckle image processing unit 24 is not particularly limited, and a known method can be adopted.

(5) Image Combination Unit

In the imaging system 201 according to the second embodiment, the image combination unit 25 that combines the speckle image processed by the speckle image processing unit 23 and the non-speckle image processed by the non-speckle image processing unit 24 is included.

In this image combination unit 25, for example, image information of the non-speckle image and image information of the speckle image are superimposed to create a speckle combination image. At this time, it is unnecessary to perform adjustment of the superimposition position such as template matching.

Figure 4:
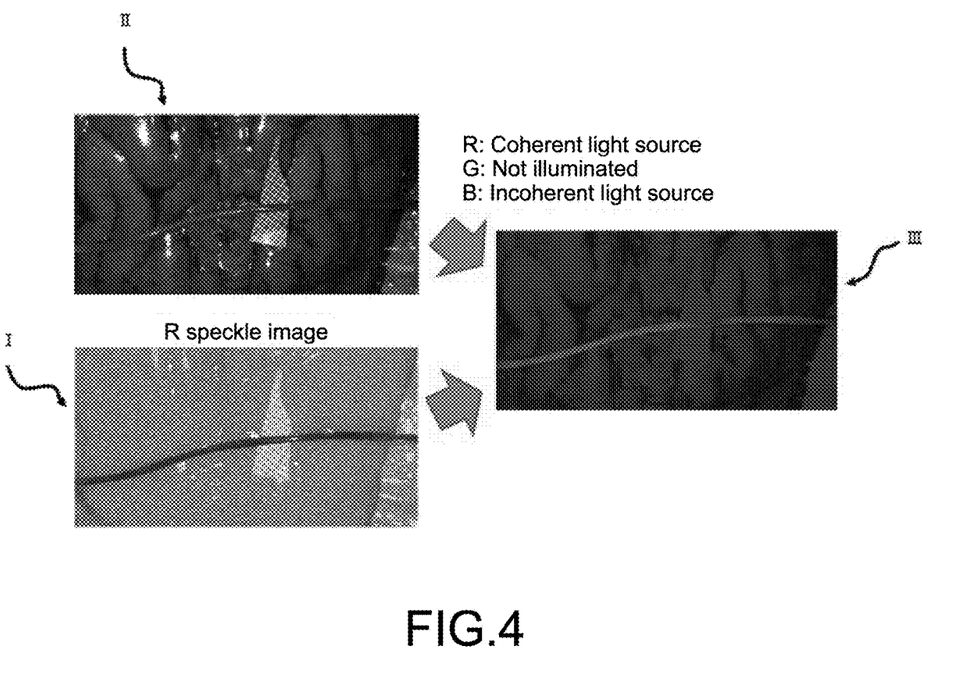
FIG. 4 is a photograph substitute diagram showing a function of an image combination unit included in the imaging system shown in FIG. 3.

Specifically, as shown in FIG. 4, a speckle image I based on red coherent light and a non-speckle image II based on blue incoherent light are superimposed to create a speckle combination image III. In such a case, as shown in FIG. 4, the speckle combination image III by which not only a scattering fluid (red part) on which the speckle is reflected but also an event (blue part) provided on the back surface of the scattering fluid by irradiation of the incoherent light can be checked is created.

Here, in order to improve the accuracy of the analysis result by the analysis unit 15, the brightness value of the speckle combination image may be corrected so that the brightness distribution in the speckle combination image III becomes uniform. This correction method is not particularly limited, and a known method can be used.

Note that the method of creating the speckle combination image is not particularly limited, and a known method can be adopted.

In accordance with the imaging system 201 according to the second embodiment configured as described above, the resolution of the speckle image can be increased by the speckle processing unit 22 and the speckle image processing unit 23, and the resolution of the non-speckle image can be increased by the non-speckle image processing unit 24. As a result, also the resolution of the speckle combination image can be increased, thereby making it possible to improve the accuracy of analyzing the state of the imaging target O.

3. Imaging Apparatus

The present technology provides also an imaging apparatus. An imaging apparatus 301 according to the present technology will be described with reference to FIG. 5. The imaging apparatus 301 roughly includes at least a first light source 110, a second light source 120, an image capturing unit 130, and a cross-talk elimination unit 140. Further, the imaging apparatus 301 may include an analysis unit 150, a storage unit 160, a display unit 170, a separation unit 180, a speckle processing unit 190, a speckle image processing unit 200, a non-speckle image processing unit 210, and an image combination unit 220 as necessary. Hereinafter, the respective units will be described.

(1) First Light Source

Figure 5:
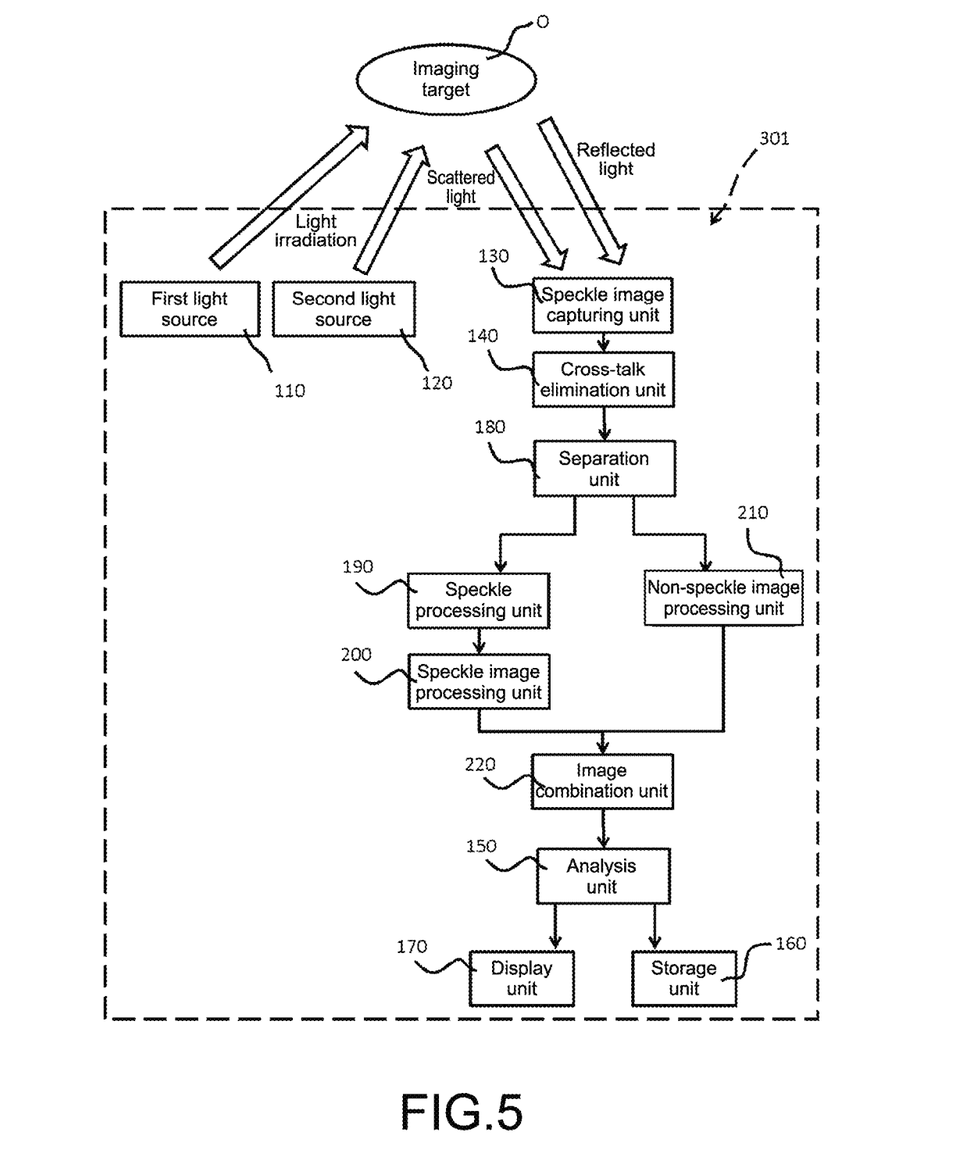
FIG. 5 is a schematic conceptual diagram schematically showing a first embodiment of an imaging apparatus according to the present technology.

The first light source 110 has the same configuration as that of the first light source 11 of the imaging system 101 according to the present technology, and irradiates the imaging target O with coherent light. The coherent light emitted from the first light source 110 represents light in which the phase relationship of light waves at arbitrary two points in the light beam temporally invariable and constant, which shows perfect coherence even when after the light beam is split by an arbitrary method, a large optical path difference is given to the split light beams and the light beams are overlapped again. It is preferable that the coherent light output from the first light source 110 according to the present technology has a wavelength band in the range of 550 to 700 nm and is red. It is more preferable that the coherent light has a wavelength band of 600 nm and is red.

The type of the first light source 110 that emits the coherent light is not particularly limited as long as the effect of the present technology is not impaired. Examples thereof include laser light. As the first light source 110 that emits laser light, for example, one or more kinds of an argon ion (Ar) laser, a helium-neon (He—Ne) laser, a dye laser, a krypton (Cr) laser, a semiconductor laser, a solid laser obtained by combining a semiconductor laser and a wavelength conversion optical device, and the like can be freely combined and used.

(2) Second Light Source

The second light source 120 has the same configuration as that of the second light source 12 of the imaging system 101 according to the present technology, and irradiates the imaging target O with the incoherent light. In the imaging apparatus 301 according to the present technology, coherent light and incoherent light are simultaneously applied to the imaging target O. That is, the second light source 120 and the first light source 110 simultaneously apply light. The incoherent light emitted from the second light source 120 is light that hardly shows coherence like object light (object wave). Here, it is preferable that the wavelength of the incoherent light is approximately the same as the wavelength of the coherent light emitted from the first light source 110. Therefore, when applying the incoherent light, it is preferable to adopt a configuration capable of adjusting the wavelength of the incoherent light by using a band-pass filter.

It is preferable that the incoherent light output from the second light source 12 according to the present technology has a wavelength band in the range of 350 to 550 nm and is blue. It is more preferable that the incoherent light has a wavelength band of 400 nm and is blue.

The type of the second light source 120 is not particularly limited as long as the effect of the present technology is not impaired. Examples thereof include a light emitting diode. Further, examples of another light source include a xenon lamp, a metal halide lamp, and a high pressure mercury lamp.

(3) Image Capturing Unit

The image capturing unit 130 has the same configuration as that of the image capturing unit 13 of the imaging system 101 according to the present technology, and captures a speckle image and a non-speckle image.

That is, the image capturing unit 130 images a speckle based on scattered light obtained from the imaging target O irradiated with the coherent light. Further, the imaging target O is imaged on the basis of reflected light obtained from the imaging target O irradiated with the incoherent light. Here, since the incoherent light is light that hardly shows coherence, a speckle that is a random interference/diffraction pattern does not occur in the captured image based on the incoherent light. Hereinafter, the captured image in which no speckle occurs will be referred to as "non-speckle image" for convenience of description.

Further, in the image capturing unit 130, the brightness distribution of the speckle in the captured speckle image may be measured. Here, when an object illuminated by using the coherent light is observed by an imaging optical system, a speckle due to scattering of the object is observed on the image surface. In this image capturing unit 130, for example, the brightness distribution of the speckle in the captured image is measured using a brightness meter. In addition, the brightness distribution of the speckle can be calculated from an image captured by an image sensor such as CCD and CMOS.

This method of measuring the brightness distribution is not particularly limited as long as the effect of the present technology is not impaired, and one or more kinds of known calculation methods can be selected and freely used in combination.

Such an imaging method performed by the image capturing unit 130 is not particularly limited as long as the effect of the present technology is not impaired, and one or more kinds of known imaging methods can be selected and freely used in combination. Examples of the imaging method include an imaging method using an image sensor such as a CCD (Charge Coupled Device) sensor and a CMOS (Complementary Metal Oxide Semiconductor) sensor.

In this image capturing unit 130, for example, an image or the like in which pseudo blood vessels through which pseudo blood is flowing are mapped on the basis of the brightness distribution of the speckle is generated. Here, since the speckle is a random interference/diffraction pattern as described above, when a scattering fluid such as blood moves or temporarily changes, also the speckle temporarily changes. Therefore, it is possible to observe the boundary between the fluid and other parts.

Note that the image capturing unit 130 may be configured to perform leveling using a plurality of speckle images, for example, to reduce the unevenness of the speckle image in order to clarify the part where a speckle occurs.

(4) Cross-Talk Elimination Unit

The cross-talk elimination unit 140 has the same configuration as that of the cross-talk elimination unit 14 of the imaging system 101 according to the present technology, and eliminates the cross-talk.

More specifically, the cross-talk elimination unit 140 is configured as a pixel unit in which pixels corresponding to respective color components including a plurality of color components are regularly arranged on a plane, and placed closer to the imaging target O than the image capturing unit 130. Then, pixel data obtained from only pixels sensitive to light (e.g., red coherent light) of a specific wavelength is used for a speckle image, and pixel data obtained from only pixels sensitive to light (e.g., blue incoherent light) of a specific wavelength is used for a non-speckle image. Such a method can be considered. In the case where the cross-talk elimination unit 140 is configured in this way, since pixels constituting the cross-talk elimination unit 140 do not receive stray light, it is possible to eliminate cross-talk as much as possible.

Examples of the specific configuration of the cross-talk elimination unit 140 include a single plate type digital imager masked with a color filter in a Bayer pattern including pixels corresponding to color components of R, G, and B. Examples of another configuration include a three-plate type digital imager.

(5) Analysis Unit

The imaging apparatus 301 according to the present technology can include the analysis unit 150 as necessary. This analysis unit 150 has the same configuration as that of the analysis unit 15 of the imaging system 101 according to the present technology, and analyzes a speckle combination image obtained by combining a speckle image and a non-speckle image from which a speckle is eliminated by the cross-talk elimination unit 140. Specifically, the state of the imaging target O is analyzed on the basis of the brightness distribution or speckle shown in the speckle combination image.

In the analysis unit 150, for example, in the case where the imaging target O is a blood vessel, when a scattering fluid such as blood moves or temporarily changes, also the speckle temporarily changes accordingly. Therefore, the analysis unit 150 is capable of measuring the velocity of blood flow.

Note that this analysis unit 150 is not essential to the imaging apparatus 301 according to the present technology, and an external analysis apparatus or the like may be used to analyze the state of the imaging target O.

(6) Storage Unit

The imaging apparatus 301 according to the present technology may include the storage unit 160 as necessary. This storage unit 16 has the same configuration as that of the storage unit 16 of the imaging system 101 according to the present technology, and stores the speckle image and the non-speckle image captured by the image capturing unit 130, an analysis result by the analysis unit 150, and the like.

This storage unit 160 is not essential to the imaging apparatus 301 according to the present technology. For example, an external storage apparatus may be connected, and the speckle image and the like may be stored therein.

(7) Display Unit

The imaging apparatus 301 according to the present technology may include the display unit 170 as necessary. This display unit 170 has the same configuration as that of the display unit 17 of the imaging system 101 according to the present technology, and the speckle image and the non-speckle image captured by the image capturing unit 130, an analysis result by the analysis unit 150, and the like are displayed thereon.

Here, on the display unit 170, the brightness distribution of the speckle measured by the image capturing unit 130 may be superimposed on the speckle image and displayed.

This display unit 170 is not essential to the imaging apparatus 301 according to the present technology. For example, an external monitor or the like may be used to irradiate the imaging target O with light.

(8) Separation Unit

The imaging apparatus 301 according to the present technology can include the separation unit 180 as necessary. The separation unit 180 has the same configuration as that of the separation unit 21 of the imaging system 101 according to the present technology, and separates image information of the captured speckle image and image information of the captured non-speckle image.

The method of separating the image information performed by the separation unit 180 is not particularly limited, and a known method can be adopted.

(9) Speckle Processing Unit

In the imaging apparatus 301 according to the present technology, predetermined processing is performed on images of the speckle image and the non-speckle image separated by the separation unit 180.

In the imaging apparatus 301, the speckle processing unit 190 and the speckle image processing unit 200 perform predetermined processing on the speckle image.

The speckle processing unit 190 converts the speckle image based on coherent light into a speckle fluid image in which the speckle flows in a predetermined direction. In such a case, examples of the method of calculating the flow of the speckle include a method of using, as an index, speckle contrast that is a value obtained by dividing the standard deviation of the intensity distribution by the average of the intensity distribution.

Then, in the speckle processing unit 190, a speckle fluid image is created by imaging the speckle contrast.

(10) Speckle Image Processing Unit

After a speckle fluid image is created by the speckle processing unit 190, the speckle image processing unit 200 inverts the speckle contrast in the speckle fluid image first. Accordingly, in the imaging target O, it is possible to equalize the value of the speckle image with the value at the point where the flow rate is high. Further, the speckle contrast is optimized. As a result, in the speckle fluid image, it is possible to maximize the speckle contrast, thereby making it possible to improve the detection accuracy of a scattering fluid such as blood.

Note that the method of inverting the speckle contrast and the method of optimizing the speckle contrast in the speckle image processing unit 200 are not particularly limited, and known methods can be adopted.

(11) Non-Speckle Image Processing Unit

In the imaging apparatus 301 according to the present embodiment, after the separation unit 180 separates a non-speckle image from a speckle image, the non-speckle image processing unit 210 performs predetermined processing on the non-speckle image.

Specifically, the brightness distribution measured by the image capturing unit 130 is optimized. As a result, since the brightness distribution for the imaging target O can be optimized in the non-speckle image, it is possible to increase the resolution of the non-speckle image.

Note that the method of optimizing the brightness distribution by the non-speckle image processing unit 210 is not particularly limited, and a known method can be adopted.

(12) Image Combination Unit

The imaging apparatus 301 according to the present technology includes the image combination unit 220 that combines the speckle image processed by the speckle image processing unit 200 and the non-speckle image processed by the non-speckle image processing unit 210.

In this image combination unit 220, for example, image information of the non-speckle image and image information of the speckle image are superimposed to create a speckle combination image. In such a case, in order to improve the accuracy of the analysis result by the analysis unit 150, the brightness value of the speckle combination image may be corrected so that the brightness distribution in the speckle combination image becomes uniform. This correction method is not particularly limited, and a known method can be used.

Note that the method of creating the speckle combination image is not particularly limited, and a known method can be adopted.

In accordance with the above-mentioned imaging apparatus 301 according to the present technology, since the cross-talk elimination unit 140 is included, the speckle image and the non-speckle image captured by the image capturing unit 13 become more clear.

As a result, for example, when blood vessels through which blood is flowing are imaged, since the speckle change according to the temporal change of blood can be observed, it is possible to acquire an image by which a flow path of blood cells can be accurately recognized. As a result, it is possible to accurately observe the relative position of blood vessels to a biological tissue (e.g., heart).

Further, in accordance with the imaging apparatus 301 according to the present technology, since a configuration in which the speckle image and the non-speckle image are captured by the single image capturing unit 130 is adopted, for example, in the case of combining the speckle image and the non-speckle image, it is possible to eliminate occurrence of positional displacement of the respective images as much as possible. As a result, it is possible to improve the resolution of the speckle combination image, thereby making it possible to analyze the imaging target O more accurately.

Further, in accordance with the imaging apparatus 301 according to the present technology, for example, in the case where the imaging target O is irradiated with red coherent light from the first light source 110 and a speckle image is captured on the basis of scattered light from the imaging target O, it is possible to enhance the capability of drawing blood flow when the imaging target O is blood in which scattering is dominant. Meanwhile, for example, in the case where the imaging target O is irradiated with blue incoherent light from the second light source 120 and a non-speckle image is captured on the basis of reflected light from the imaging target O, it is possible to enhance the capability of drawing blood vessels when the imaging target O is a blood vessel, because blue light is easily absorbed by the blood.

Further, in the imaging apparatus 301 according to the present technology, the resolution of the speckle image can be increased by the speckle processing unit 190 and the speckle image processing unit 200, and the resolution of the non-speckle image can be increased by the non-speckle image processing unit 210. As a result, also the resolution of the speckle combination image can be increased, thereby making it possible to improve the accuracy of analyzing the state of the imaging target O.

4. Imaging Method

Figure 6:
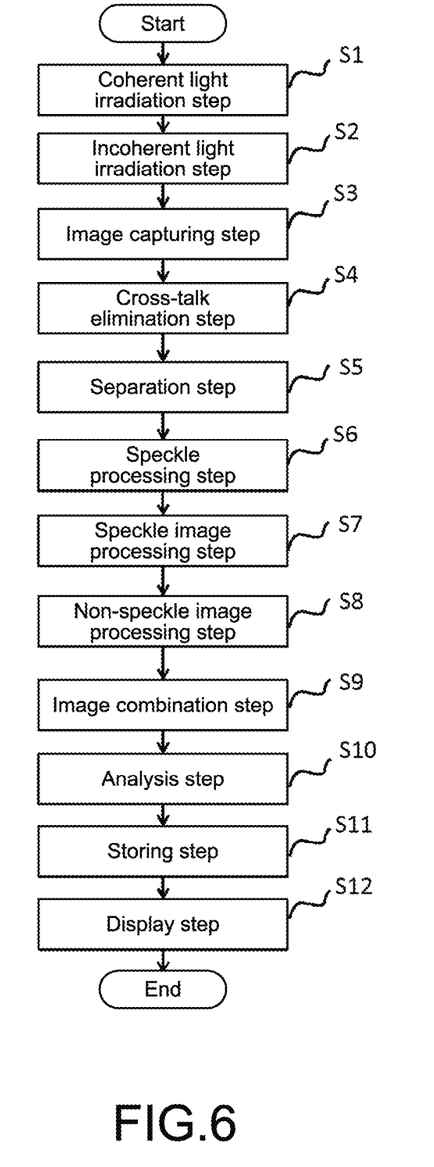
FIG. 6 is a flowchart showing an imaging method according to the present technology.

FIG. 6 is a flowchart showing an imaging method according to the present technology. An imaging method according to the first embodiment includes at least a coherent light irradiation step, an incoherent light irradiation step, an image capturing step, and a cross-talk elimination step, and may include a separation step, a speckle processing step, a speckle image processing step, a non-speckle image processing step, an image combination step, an analysis step, a storing step, and a display step as necessary.

Note that in FIG. 6, although the separation step, the speckle processing step, the speckle image processing step, the non-speckle image processing step, the image combination step, the analysis step, the storing step, and the display step are also shown, these steps are not essential as described above, and are therefore not necessarily performed in the imaging method according to the present technology.

However, since predetermined effects are exerted by including the separation step, the speckle processing step, the speckle image processing step, the non-speckle image processing step, the image combination step, the analysis step, the storing step, and the display step, it is preferable to include these steps. The respective steps will be described below in the order of executing the imaging method according to the present technology.

(1) Coherent Light Irradiation Step

In the imaging method according to the present technology, a coherent light irradiation step S1 of irradiating the imaging target O with coherent light is performed first. It is preferable that the coherent light irradiated in the coherent light irradiation step has a wavelength band in the range of 550 to 700 nm and is red. It is more preferable that the coherent light has a wavelength band of 600 nm and is red.

The type of the light source that can be used in the coherent light irradiation step S1 is not particularly limited as long as the effect of the present technology is not impaired. Examples thereof include laser light. As the light source, for example, one or more kinds of an argon ion (Ar) laser, a helium-neon (He—Ne) laser, a dye laser, a krypton (Cr) laser, a semiconductor laser, a solid laser obtained by combining a semiconductor laser and a wavelength conversion optical device, and the like can be freely combined and used.

(2) Incoherent Light Irradiation Step

In the imaging method according to the present technology, the imaging target O is irradiates with incoherent light simultaneously with the coherent light irradiation step S1. Here, the kind of the incoherent light source is not particularly limited as long as the effect of the present technology is not impaired. Examples thereof include a light emitting diode. Further, examples of another light source include a xenon lamp, a metal halide lamp, and a high pressure mercury lamp.

It is preferable that the incoherent light irradiated in the incoherent light irradiation step has a wavelength band in the range of 350 to 550 nm and is blue. It is more preferable that the incoherent light has a wavelength band of 400 nm and is blue.

(3) Image Capturing Step

In the imaging method according to the present technology, an image capturing step S3 is performed after the coherent light irradiation step S1 and the incoherent light irradiation step S2 are performed.

In this image capturing step S3, a single image sensor is used for capturing a speckle image and a non-speckle image. Specifically, a speckle is imaged on the basis of scattered light obtained from the imaging target O irradiated with the coherent light. Further, a non-speckle image in which no speckle is projected, i.e., a bright field image is captured on the basis of reflected light obtained from the imaging target O irradiated with the incoherent light.

In this image capturing step S3, for example, an image or the like in which pseudo blood vessels through which pseudo blood is flowing are mapped on the basis of the brightness distribution of the speckle is generated. Here, since the speckle is a random interference/diffraction pattern as described above, when a scattering fluid such as blood moves or temporarily changes, also the speckle temporarily changes. Therefore, it is possible to observe the boundary between the fluid and other parts.

Here, the imaging method in the image capturing step S3 is not particularly limited, and one or more kinds of known imaging methods can be selected and freely used in combination. Examples of the imaging method include an imaging method using an image sensor such as a CCD (Charge Coupled Device) sensor and a CMOS (Complementary Metal Oxide Semiconductor) sensor. Further, in the image capturing step S3, in order to clarify the part where a speckle occurs, it may be possible to perform leveling using a plurality of speckle images, for example, to reduce the unevenness of the speckle image.

(4) Cross-Talk Elimination Step

In the imaging method according to the present technology, a cross-talk elimination step S4 of eliminating cross-talk as much as possible by using a predetermined image sensor is performed after the speckle image and the non-speckle image are captured.

As the image sensor, a pixel unit in which pixels corresponding to respective color components including a plurality of color components are regularly arranged on a plane can be used. Examples thereof include a single plate type digital imager masked with a color filter in a Bayer pattern including pixels corresponding to color components of R, G, and B. Examples of another configuration include a three-plate type digital imager.

Then, in the cross-talk elimination step S4, the coherent light and the incoherent light are applied via the image sensor, pixel data obtained from only pixels sensitive to light (e.g., red coherent light) of a specific wavelength is used for a speckle image, and pixel data obtained from only pixels sensitive to light (e.g., blue incoherent light) of a specific wavelength is used for a non-speckle image. Such a method can be considered. In accordance with such a cross-talk elimination step S4, since pixels do not receive stray light, it is possible to eliminate cross-talk as much as possible.

(5) Separation Step

In the imaging method according to the present technology, image information of the captured speckle image and image information of the non-speckle image are separated after cross-talk is eliminated in the cross-talk elimination step S4. The method of separating the image information is not particularly limited, and a known method can be adopted.

(6) Speckle Processing Step

In the imaging method according to the present technology, the speckle image separated in the separation step S5 is subjected to a speckle processing step S6.

In this speckle processing step S6, the speckle image captured on the basis of the coherent light is converted into a speckle fluid image in which the speckle flows.

Specifically, the flow of the speckle in the speckle image is calculated. Examples of the calculation method include a method of using, as an index, speckle contrast that is a value obtained by dividing the standard deviation of the intensity distribution by the average of the intensity distribution. Then, a speckle fluid image is created by imaging the speckle contrast.

(7) Speckle Image Processing Step

In the imaging method according to the present technology, a speckle image processing step S7 is performed on the speckle fluid image after the speckle processing step S6 is performed.

In this speckle image processing step S7, the speckle contrast is inverted first in the speckle fluid image. Accordingly, in the imaging target O, it is possible to equalize the value of the speckle image with the value at the point where the flow rate is high. After that, the speckle contrast is optimized. As a result, in the speckle fluid image, it is possible to maximize the speckle contrast, thereby making it possible to improve the detection accuracy of a scattering fluid such as blood.

Note that the method of inverting the speckle contrast and the method of optimizing the speckle contrast in the speckle image processing step S7 are not particularly limited, and known methods can be adopted.

(8) Non-Speckle Image Processing Step

In the imaging method according to the present technology, a non-speckle image processing step S8 is performed.

That is, after the non-speckle image is separated from the speckle image in the separation step S5, predetermined processing is performed on the non-speckle image in the non-speckle image processing step S8. Note that although FIG. 6 shows that the non-speckle image processing step S8 is performed after the speckle image processing step S7, the non-speckle image processing step S8 is performed in parallel with the speckle processing step S6 after the separation step S5.

Specifically, the brightness distribution measured at the time of the image capturing step S3 is optimized. As a result, since the brightness distribution for the imaging target O can be optimized in the non-speckle image, it is possible to increase the resolution of the non-speckle image. Here, the method of optimizing the brightness distribution is not particularly limited, and a known method can be adopted.

(9) Image Combination Step

The imaging method according to the present technology includes an image combination step S9 of combining the speckle image subjected to the speckle image processing step S7 and the non-speckle image subjected to the non-speckle image processing step S8.

In this image combination step S9, for example, image information of the non-speckle image and image information of the speckle image are superimposed to create a speckle combination image. In such a case, in order to improve the accuracy of the analysis result by the analysis step described below, the brightness value of the speckle combination image may be corrected so that the brightness distribution in the speckle combination image becomes uniform. This correction method is not particularly limited, and a known method can be used.

Note that the method of creating the speckle combination image is not particularly limited, and a known method can be adopted.

(10) Analysis Step

The imaging method according to the present technology may include an analysis step S10 as necessary. In the analysis step S10, the speckle combination image created in the image combination step S9 is analyzed. Specifically, the state of the imaging target O is analyzed on the basis of the brightness distribution or speckle shown in the speckle combination image.

In the analysis step S10, for example, in the case where the imaging target O is a blood vessel, when a scattering fluid such as blood moves or temporarily changes, also the speckle temporarily changes accordingly. Therefore, in the analysis step S10, the velocity of blood flow can be measured.

(11) Storing Step

The imaging method according to the present technology may include a storing step S11 as necessary.

In this storing Step S11, the speckle image subjected to the speckle processing step S6 and the speckle image processing step S7, the non-speckle image subjected to the non-speckle image processing step S8, the speckle combination image created in the image combination step S9, the analysis result in the analysis step S10, and the like are stored.

(12) Display Step

The imaging method according to the present technology may include a display step S12 as necessary.

In this display step S12, the speckle image subjected to the speckle processing step S6 and the speckle image processing step S7, the non-speckle image subjected to the non-speckle image processing step S8, the speckle combination image created in the image combination step S9, the analysis result in the analysis step S10, and the like are displayed.

In accordance with the above-mentioned imaging method according to the present technology, since the cross-talk elimination step is included, it is possible to improve the resolution of the speckle image and the non-speckle image captured in the image capturing step S3.

As a result, for example, when blood vessels through which blood is flowing are imaged, since the speckle change according to the temporal change of blood can be observed, it is possible to acquire an image by which a flow path of blood cells can be accurately recognized. As a result, it is possible to accurately observe the relative position of blood vessels to a biological tissue (e.g., heart).

Further, in accordance with the imaging method according to the present technology, for example, in the case where the imaging target O is irradiated with red coherent light in the coherent light irradiation step S1 and a speckle image is captured on the basis of scattered light from the imaging target O, it is possible to enhance the capability of drawing blood flow when the imaging target O is blood in which scattering is dominant. Meanwhile, for example, in the case where the imaging target O is irradiated with blue incoherent light in the incoherent light irradiation step S2 and a non-speckle image is captured on the basis of reflected light from the imaging target O, it is possible to enhance the capability of drawing blood vessels when the imaging target O is a blood vessel, because blue light is easily absorbed by the blood.

Further, in the case where the imaging method according to the present technology includes the speckle processing step S6 and the speckle image processing step S7, it is possible to increase the resolution of the speckle image, and increase the resolution of the non-speckle image in the case of including the non-speckle image processing step S8. As a result, it is possible to increase also the resolution of the speckle combination image, thereby making it possible to improve the accuracy of analyzing the state of the imaging target O.

It should be noted that the present technology may take the following configurations.

(1)

An imaging system, including:

a first light source that irradiates an imaging target with coherent light of a first wavelength band;

a second light source that irradiates the imaging target with incoherent light of a second wavelength band;

an image capturing unit that captures a speckle image and a non-speckle image, the speckle image being obtained from scattered light of the imaging target irradiated with the coherent light, the non-speckle image being obtained from reflected light of the imaging target irradiated with the incoherent light; and a cross-talk elimination unit that eliminates cross-talk that occurs between the captured speckle image and the captured non-speckle image.

(1)

The imaging system according to (1), in which the first light source is a red light source, and the second light source is a blue light source.

(3)

The imaging system according to (1) or (2), in which the wavelength band of the coherent light is 550 to 700 nm, and the wavelength band of the incoherent light is 350 to 550 nm.

(4)

The imaging system according to any one of (1) to (3), in which the second light source irradiates the imaging target with the incoherent light simultaneously with the irradiation by the first light source.

(5)

The imaging system according to any one of (1) to (4), further including a separation unit that separates the captured speckle image and the captured non-speckle image.

(6)

The imaging system according to any one of (1) to (5), further including an image combination unit that combines the separated speckle image and the separated non-speckle image.

(7)

The imaging system according to any one of (1) to (6), in which the image capturing unit includes a pixel unit in which pixels corresponding to respective color components including a plurality of color components are regularly arranged on a plane.

(8)

The imaging system according to (7), in which the pixel unit has a Bayer pattern.

Further, the present technology can provide also the following imaging apparatus.

(9)

An imaging apparatus, including:

a first light source that irradiates an imaging target with coherent light of a first wavelength band;

a second light source that irradiates the imaging target with incoherent light of a second wavelength band;

an image capturing unit that captures a speckle image and a non-speckle image, the speckle image being obtained from scattered light of the imaging target irradiated with the coherent light, the non-speckle image being obtained from reflected light of the imaging target irradiated with the incoherent light; and a cross-talk elimination unit that eliminates cross-talk that occurs between the captured speckle image and the captured non-speckle image.

(10)

The imaging apparatus according to (9), in which the first light source is a red light source, and the second light source is a blue light source.

(11)

The imaging apparatus according to (9) or (10), in which the wavelength band of the coherent light is 550 to 700 nm, and the wavelength band of the incoherent light is 350 to 550 nm.

(12)

The imaging apparatus according to any one of (9) to (11), in which the second light source irradiates the imaging target with the incoherent light simultaneously with the irradiation by the first light source.

(13)

The imaging apparatus according to any one of (9) to (12), further including a separation unit that separates the captured speckle image and the captured non-speckle image.

(14)

The imaging apparatus according to any one of (9) to (13), further including an image combination unit that combines the separated speckle image and the separated non-speckle image.

(15)

The imaging apparatus according to any one of (9) to (14), in which the image capturing unit includes a pixel unit in which pixels corresponding to respective color components including a plurality of color components are regularly arranged on a plane.

(16)

The imaging apparatus according to (15), in which the pixel unit has a Bayer pattern.

The present technology can provide also the following imaging method.

(17)

An imaging method, including:

a coherent light irradiation step of irradiating an imaging target with coherent light of a first wavelength band;

an incoherent light irradiation step of irradiating the imaging target with incoherent light of a second wavelength band;

a speckle image capturing step of capturing a speckle image obtained from scattered light of the imaging target irradiated with the coherent light;

a non-speckle image capturing step of capturing a non-speckle image obtained from reflected light of the imaging target irradiated with the incoherent light; and a cross-talk elimination step of eliminating cross-talk that occurs between the captured speckle image and the captured non-speckle image.

(18)

The imaging method according to (17), in which the first light source is a red light source, and the second light source is a blue light source.

(19)

The imaging method according to (17) or (18), in which the wavelength band of the coherent light is 550 to 700 nm, and the wavelength band of the incoherent light is 350 to 550 nm.

(20)

The imaging method according to any one of (17) to (19), in which the coherent light irradiation step and the incoherent light irradiation step are simultaneously performed.

(21)

The imaging method according to any one of (17) to (20), further including a separation step of separating the captured speckle image and the captured non-speckle image.

(22)

The imaging method according to any one of (17) to (21), further including an image combination step of combining the separated speckle image and the separated non-speckle image.

REFERENCE SIGNS LIST 101, 201 imaging system
301 imaging apparatus
11, 110 first light source
12, 120 second light source
13, 130 image capturing unit
14, 140 cross-talk elimination unit 14
15, 150 analysis unit
16, 160 storage unit
17, 170 display unit
21, 180 separation unit
22, 190 speckle processing unit
23, 200 speckle image processing unit
24, 210 non-speckle image processing unit
25, 220 image combination unit

The invention claimed is:

1. An imaging system, comprising:

a first light source configured to irradiate an imaging target with coherent light of a first wavelength band;

a second light source configured to irradiate the imaging target with incoherent light of a second wavelength band;

an image capturing unit configured to capture a speckle image and a non-speckle image, wherein the speckle image is obtained from scattered light of the imaging target irradiated with the coherent light, and the non-speckle image is obtained from reflected light of the imaging target irradiated with the incoherent light; and a cross-talk elimination unit configured to eliminate cross-talk that occurs between the captured speckle image and the captured non-speckle image, wherein the image capturing unit is a pixel unit in which a plurality of pixels, corresponding to respective color components from a plurality of color components, are regularly arranged on a plane.

2. The imaging system according to claim 1, wherein the first light source is a red light source, and the second light source is a blue light source.

3. The imaging system according to claim 2, wherein the first wavelength band of the coherent light is 550 nm (nanometer) to 700 nm, and the second wavelength band of the incoherent light is 350 nm to 550 nm.

4. The imaging system according to claim 1, wherein the second light source is configured to irradiate the imaging target with the incoherent light concurrently with the irradiation by the first light source.

5. The imaging system according to claim 1, further comprising a separation unit configured to separate the captured speckle image and the captured non-speckle image.

6. The imaging system according to claim 5, further comprising an image combination unit configured to combine the separated speckle image and the separated non-speckle image.

7. The imaging system according to claim 1, wherein the cross-talk elimination unit has a Bayer pattern.

8. The imaging system according to claim 1, wherein the imaging target includes a fluid.

9. The imaging system according to claim 1, wherein the imaging target includes a biological tissue.

10. The imaging system according to claim 1, wherein the imaging target is a heart.

11. The imaging system according to claim 1, wherein the imaging target includes a blood vessel and blood.

12. The imaging system according to claim 1, wherein the coherent light and the incoherent light are guided into a surgical apparatus.

13. The imaging system according to claim 1, wherein the coherent light and the incoherent light are guided into one of a microscope or an endoscope.

14. An imaging apparatus, comprising:
a first light source configured to irradiate an imaging target with coherent light of a first wavelength band;
a second light source configured to irradiate the imaging target with incoherent light of a second wavelength band;
an image capturing unit configured to capture a speckle image and a non-speckle image, wherein
the speckle image is obtained from scattered light of the imaging target irradiated with the coherent light, and
the non-speckle image is obtained from reflected light of the imaging target irradiated with the incoherent light; and
a cross-talk elimination unit configured to eliminate cross-talk that occurs between the captured speckle image and the captured non-speckle image,
wherein the image capturing unit is a pixel unit in which a plurality of pixels, corresponding to respective color components from a plurality of color components, are regularly arranged on a plane.

15. The imaging apparatus according to claim 14, wherein the first light source is a red light source, and the second light source is a blue light source.

16. The imaging apparatus according to claim 15, wherein the first wavelength band of the coherent light is 550 nm (nanometer) to 700 nm, and the second wavelength band of the incoherent light is 350 nm to 550 nm.

17. The imaging apparatus according to claim 14, wherein the second light source is configured to irradiate the imaging target with the incoherent light concurrently with the irradiation by the first light source.

18. The imaging apparatus according to claim 14, further comprising a separation unit configured to separate the captured speckle image and the captured non-speckle image.

19. The imaging apparatus according to claim 18, further comprising an image combination unit configured to combine the separated speckle image and the separated non-speckle image.

20. The imaging apparatus according to claim 14, wherein the cross-talk elimination unit has a Bayer pattern.

21. An imaging method, comprising:
in an imaging system:
irradiating, by a first light source of the imaging system, an imaging target with coherent light of a first wavelength band;
irradiating, by a second light source of the imaging system, the imaging target with incoherent light of a second wavelength band;
capturing, by an image capturing unit of the imaging system, a speckle image obtained from scattered light of the imaging target irradiated with the coherent light;
capturing, by the image capturing unit, a non-speckle image obtained from reflected light of the imaging target irradiated with the incoherent light; and
eliminating, by a cross-talk elimination unit of the imaging system, cross-talk that occurs between the captured speckle image and the captured non-speckle image,
wherein the image capturing unit is a pixel unit in which a plurality of pixels, corresponding to respective color components from a plurality of color components, are regularly arranged on a plane.

22. The imaging method according to claim 21, wherein the coherent light is red light, and the incoherent light is blue light.

23. The imaging method according to claim 22, wherein the first wavelength band of the coherent light is 550 nm (nanometer) to 700 nm, and the second wavelength band of the incoherent light is 350 nm to 550 nm.

24. The imaging method according to claim 21, wherein the irradiation of the imaging target with the coherent light is executed concurrently with the irradiation of the imaging target with the incoherent light.

25. The imaging method according to claim 21, further comprising separating the captured speckle image and the captured non-speckle image.

26. The imaging method according to claim 25, further comprising combining the separated speckle image and the separated non-speckle image.

* * * * *